(12) United States Patent
Ledden

(10) Patent No.: US 10,371,643 B2
(45) Date of Patent: Aug. 6, 2019

(54) LUMINESCENT OXYGEN CHANNELING IMMUNOASSAYS

(71) Applicant: Siemens Healthcare Diagnostics Inc., Tarrytown, NY (US)

(72) Inventor: David J. Ledden, Medway, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 528 days.

(21) Appl. No.: 14/775,348

(22) PCT Filed: Mar. 14, 2014

(86) PCT No.: PCT/US2014/027208
§ 371 (c)(1),
(2) Date: Sep. 11, 2015

(87) PCT Pub. No.: WO2014/152322
PCT Pub. Date: Sep. 25, 2014

(65) Prior Publication Data
US 2016/0033417 A1    Feb. 4, 2016

Related U.S. Application Data

(60) Provisional application No. 61/788,194, filed on Mar. 15, 2013.

(51) Int. Cl.
G01N 33/58   (2006.01)
G01N 21/76   (2006.01)
F21K 2/06    (2006.01)
B01L 3/00    (2006.01)

(52) U.S. Cl.
CPC ............ G01N 21/76 (2013.01); B01L 3/5027 (2013.01); F21K 2/06 (2013.01); G01N 33/582 (2013.01)

(58) Field of Classification Search
CPC ........ C12Q 1/28; C12Q 1/66; G01N 33/5306; G01N 33/582; G01N 21/76
See application file for complete search history.

(56) References Cited

U.S. PATENT DOCUMENTS

| | | | |
|---|---|---|---|
| 4,277,437 A | 7/1981 | Maggio | |
| 5,340,716 A | 8/1994 | Ullman et al. | |
| 5,807,675 A * | 9/1998 | Davalian | C07D 311/20 435/6.11 |
| 2002/0197649 A1* | 12/2002 | Singh | C12Q 1/6823 435/7.1 |
| 2005/0069895 A1* | 3/2005 | Woudenberg | C12Q 1/6816 435/6.11 |

(Continued)

FOREIGN PATENT DOCUMENTS

| | | |
|---|---|---|
| EP | 0515194 A2 | 11/1992 |
| WO | 02097112 A2 | 12/2002 |

(Continued)

OTHER PUBLICATIONS

European Search Report and Written Opinion of European Application No. 14768031 dated Oct. 24, 2016.
J. M. Aubry, "Search for singlet oxygen in the decomposition of hydrogen peroxide by mineral compounds in aqueous solutions", J. Am. Chem. Soc., 1985, 107 (21), pp. 5844-5849.

(Continued)

*Primary Examiner* — Christopher L Chin
(74) *Attorney, Agent, or Firm* — Kyle D. Petaja

(57) ABSTRACT

A chemiluminescent detection system, kits and microfluidics devices containing same, and methods of use thereof, are disclosed.

16 Claims, 2 Drawing Sheets

(56) References Cited

U.S. PATENT DOCUMENTS

| | | | |
|---|---|---|---|
| 2005/0118727 A1* | 6/2005 | Schelp | G01N 33/533 436/518 |
| 2007/0020678 A1 | 1/2007 | Ault-Riche et al. | |
| 2007/0112180 A1* | 5/2007 | Gray | C12Q 1/26 530/391.7 |
| 2007/0141658 A1* | 6/2007 | Chang | C07F 5/025 435/23 |
| 2008/0164154 A1 | 7/2008 | Purvis | |
| 2008/0220434 A1* | 9/2008 | Thomas | G01N 33/536 435/6.12 |
| 2009/0068637 A1 | 3/2009 | Xia et al. | |
| 2011/0039763 A1* | 2/2011 | Eckert | A61K 8/64 514/2.4 |
| 2011/0053289 A1 | 3/2011 | Lowe et al. | |
| 2013/0041236 A1 | 2/2013 | Pugia et al. | |
| 2013/0084652 A1* | 4/2013 | Shapir | C12Q 1/28 436/501 |
| 2014/0308690 A1 | 10/2014 | Samproni | |

FOREIGN PATENT DOCUMENTS

| | | | |
|---|---|---|---|
| WO | 2009146166 A2 | 12/2009 | |
| WO | 2011143606 A1 | 11/2011 | |
| WO | WO-2011143606 A1 * | 11/2011 | C12Q 1/28 |
| WO | 2014151450 A1 | 9/2014 | |

OTHER PUBLICATIONS

J. M. Aubry et al., "Chemical sources of singlet oxygen. 3. Peroxidation of water-soluble singlet oxygen carriers with the hydrogen peroxide-molybdate system", J. Org. Chem., 1989, 54 (3), pp. 726-728.

Boehme et al., "Generation of Singlet Oxygen from Hydrogen Peroxide Disproportionation Catalyzed by Molybdate Ions", 1992, Inorg. Chem., 31, pp. 3468-3471.

Niu et al., "Singlet molecular oxygen generation from the decomposition of sodium peroxotungstate and sodium peroxomolybdate", Inorg. Chem., 1992, 31 (16), pp. 3472-3476.

Nardello et al., "95Mo NMR and kinetic studies of peroxomolybdic intermediates involved in the catalytic disproportionation of hydrogen peroxide by molybdate ions", Inorg. Chem., 1995, 34 (20), pp. 4950-4957.

Aubry et al., "Preparative Oxidation of Organic Compounds in Microemulsions with Singlet Oxygen Generated Chemically by the Sodium Molybdate/Hydrogen Peroxide System", J. Am. Chem. Soc., 1997, 119 (23), pp. 5286-5294.

Almeida et al., "Direct evidence of singlet molecular oxygen [O 2 ( 1 Δ g )] production in the reaction of acetonitrile with hydrogen peroxide in alkaline solutions", 2003, Analytica Chimica Acta, 482(1), pp. 99-104.

International Search Report and Written Opinion of International Application No. PCT/US2014/027208 dated Jul. 17, 2014.

* cited by examiner

LUMINESCENT OXYGEN CHANNELING IMMUNOASSAYS

CROSS REFERENCE TO RELATED APPLICATIONS/INCORPORATION BY REFERENCE STATEMENT

This application is the US National Stage of International Application No. PCT/US2014/027208, filed Mar. 14, 2014 and claims the benefit thereof. The International Application claims the benefit of U.S. Provisional Application No. 61/788,194, filed Mar. 15, 2013. All of the applications are incorporated by reference herein in their entirety.

BACKGROUND

Immunoassay technologies are widely used in the field of medical diagnostics. One example of a commercially used immunoassay is the induced luminescence immunoassay (LOCI®) technology. The induced luminescence immunoassay is described in U.S. Pat. No. 5,340,716 (Ullman), the entire contents of which are expressly incorporated herein by reference. The currently available LOCI® technology involves a homogeneous assay (i.e., no wash steps involved) that has high sensitivity, and the assay uses several reagents and requires that two of these reagents (referred to as a "sensibead" and a "chemibead") held by other immunoassay reagents to be in dose proximity to achieve a signal. Upon exposure to light at a certain wavelength, the sensibead releases singlet oxygen, and if the two beads are in dose proximity, the singlet oxygen is transferred to the chemibead; this causes a chemical reaction that results in the chemibead giving off light that can be measured at a different wavelength.

However, there are obstacles that exist for this technology. There are multiple factors that can contribute to background signal, such as but not limited to, (1) the nonspecifically binding of two beads to one another, and (2) the presence of two unattached beads that are simply in close proximity to one another. For these reasons, the final reaction mixture is diluted prior to light exposure to dissociate nonspecifically bound beads and to increase the mean particle distance between unbound beads, in addition, as the assay is homogeneous, plasma separation is required, and thus whole blood cannot be directly used in this diagnostic platform.

The presently disclosed and claimed inventive concept(s) is directed to new and improved compositions, assays, and methods of production and use thereof; this technology provides a heterogeneous assay format in which background signal is reduced and plasma separation is not required.

DETAILED DESCRIPTION

Figure 1:
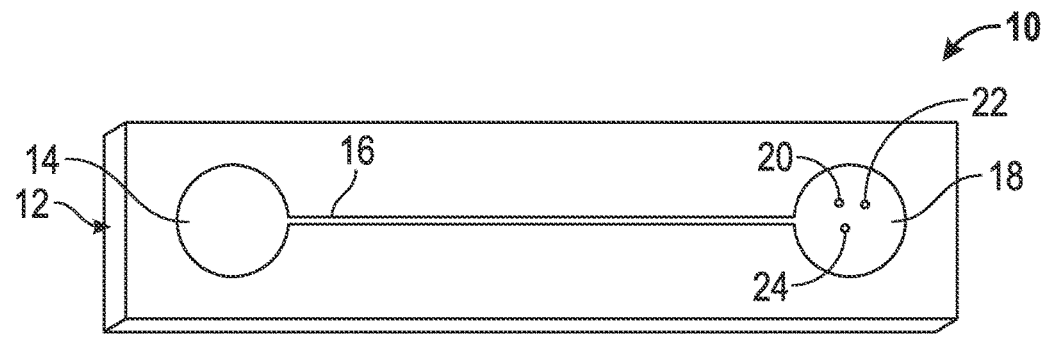
FIG. 1 illustrates one embodiment of a microfluidics device constructed in accordance with the presently disclosed and claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and claimed inventive concept(s) have been described in terms of particular embodiments, it will be apparent to those of skill in the art that variations may be applied to the compositions and/or methods and in the steps or in the sequence of steps of the method described herein without departing from the concept, spirit, and scope of the presently disclosed and claimed inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the phrase "associated with" includes covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The term "purified" as used herein means at least one order of magnitude of purification is achieved compared to the starting material or of the natural material for example but not by way of limitation, two, three, four, or five orders of magnitude of purification of the starting material or of the natural material. Thus, the term "purified" as utilized herein does not necessarily mean that the material is 100 % purified, and therefore such term does not exclude the presence of other material(s) present in the purified composition.

Throughout the specification and claims, unless the context requires otherwise, the terms "substantially" and "about" will be understood to not be limited to the specific terms qualified by these adjectives/adverbs, but allow for minor variations and/or deviations that do not result in a significant impact thereto. For example, in certain instances the term "about" is used to indicate that a value includes the inherent variation of error for the device, the method being employed to determine the value and/or the variation that exists among study subjects. Similarly, the term "substantially" may also relate to 80 % or higher, such as 85 % or higher, or 90 % or higher, or 95 % or higher, or 99 % or higher, and the like.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, halogenid selected from fluoride, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocycloalkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocycloalkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)2, carboxy, and —C(O))-alkyl.

In particular embodiments, the term "analog" as used herein refers to a compound that binds to the same binding partner (i.e., antibody) as a target analyte but that is chemically different from the target analyte. For example but not by way of limitation, when the target analyte is a peptide, polypeptide, or protein, the target analyte may possess an epitope to which a binding partner binds (i.e., for indirect association of the singlet oxygen-activatable chemiluminescent composition and/or sensitizer with the target analyte). In this example, an analog of the target analyte possesses an epitope that is identical to the epitope of the target analyte that is recognized by the binding partner; therefore, the analog is capable of binding to the binding partner to which the target analyte binds, even through the analyte may have a different amino acid sequence than the target analyte and thus be less than 100 % identical thereto.

The term "sample" as used herein will be understood to include any type of biological sample that may be utilized in accordance with the presently disclosed and claimed inventive concept(s). Examples of biological samples that may be utilized include, but are not limited to, whole blood or any portion thereof, plasma, serum, saliva, sputum, cerebrospinal fluid (CSF), skin, interstitial fluids, tears, mucus, urine, swabs, and the like.

The term "binding partner" as used herein will be understood to refer to any molecule capable of associating with another molecule. For example but not by way of limitation, the binding partner may be an antibody (including polyclonal or monoclonal antibodies), antibody fragments (such as but not limited to, Fab, Fab', F(ab')$_2$Fv, scFv, Fd, diabodies, single-chain antibodies, and other antibody fragments that retain at least a portion of the variable region of an intact antibody), a receptor, a ligand, aptamers, antibody substitute proteins or peptides (i.e., engineered binding proteins/peptides), molecular imprinted polymers (i.e., inorganic matrices), combinations or derivatives thereof, as well as any other molecules capable of specific binding to the analyte.

Turning now to particular embodiments of the presently claimed and disclosed inventive concept(s), assay compositions as well as kits containing same and methods of use thereof are disclosed. In some assay embodiments, signal producing system (sps) members comprise a sensitizer such as, for example, a photosensitizer, and a chemiluminescent composition where activation of the sensitizer results in a product that activates the chemiluminescent composition. One sps member usually generates a detectable signal that relates to the amount of bound and/or unbound sps member, i.e., the amount of sps member bound or not bound to the analyte being detected or to an agent that reflects the amount of the analyte to be detected. An exemplary embodiment of an assay platform on which the presently disclosed and claimed inventive concept(s) is based is the induced luminescence immunoassay (LOCI®). The induced luminescence immunoassay is described in U.S. Pat. No. 5,340,716 (Ullman), the entire contents of which are expressly incorporated herein by reference.

The presently disclosed and claimed inventive concept(s) includes a composition containing a chemiluminescent detection system. In certain embodiments, the composition includes at least three components: (a) a composition comprising a singlet oxygen-activatable chemiluminescent compound capable of directly or indirectly binding to the target analyte; (b) a sensitizer capable of directly or indirectly binding to a target analyte and capable of generating singlet oxygen in its excited state; and (c) a composition comprising a singlet oxygen quencher capable of directly or indirectly binding to unbound sensitizer. In other embodiments, the composition includes at least two components: (a) a composition capable of directly or indirectly binding to the target analyte and including both a singlet oxygen-activatable chemiluminescent compound and a sensitizer capable of generating singlet oxygen in its excited state; and (b) a composition comprising a singlet oxygen quencher capable of specifically binding to unbound sensitizer, wherein the composition binds to unbound sensitizer. In this second embodiment, the singlet oxygen-activatable chemiluminescent compound and the sensitizer are disposed together in a single composition; this composition may be in the form of a unibead or similar formulation.

In other embodiments, the composition contains a competitive chemiluminescent detection system. In these embodiments, target analyte or an analog thereof is bound to either the sensitizer- or the composition comprising the singlet oxygen-activatable chemiluminescent compound. The other reagent is capable of directly or indirectly binding to the target analyte or analog thereof bound to the sensitizer/chemiluminescent composition or to target analyte present in a sample.

Any of the compositions described herein above or otherwise contemplated herein may further include a wash solution. In addition, any of the compositions described herein above or otherwise contemplated herein may also include a microfluidics device in which the above-listed components (and/or the wash solution) are disposed.

It is to be understood that the sensitizer may be provided with multiple binding sites thereon, whereby the composition comprising the singlet oxygen quencher is capable of specifically binding (either directly or indirectly) to any unbound binding site on the sensitizer (including unbound binding sites present on both complexed and uncomplexed sensitizers).

A sensitizer is a molecule, usually a compound, for generation of a reactive intermediate such as, for example, singlet oxygen, for activation of a chemiluminescent compound. In some embodiments, the sensitizer is a photosensitizer. Other sensitizers that can be chemi-activated (by, e.g., enzymes and metal salts) include, by way of example and not limitation, other substances and compositions that can produce singlet oxygen with or without activation by an external light source. For example, certain compounds have been shown to catalyze the conversion of hydrogen peroxide to singlet oxygen and water. Non-limiting examples of other sensitizer substances and compositions include oxides of the alkaline earth metals Ca, Sr, and Ba: derivatives of elements of groups 3 A, 4 A, 5 A, and 6 A in $d^0$ configuration; oxides of actinides and lanthanides; and oxidizers $ClO^-$, $BrO^-$, $Au^{3+}$, $IO_3^-$ and $IO_4^-$; and in particular, molybdate, peroxomolybdate, tungstate, and peroxotungstate ions, and acetonitrile. The following references, which are hereby expressly incorporated by reference in their entirety, provide further disclosure regarding sensitizer substances and compositions that also fall within the scope of the presently disclosed and claimed inventive concept: Aubry, *J. Am. Chem. Soc.*, 107: 5844-5849 (1985 ), Aubry, *J. Org. Chem.*, 54:726-728 (1989 ); Bohme and Brauer, *Inorg. Chem.*, 31:3468-3471 (1992 ); Niu and Foote, *Inorg. Chem.*, 31:3472-3476 (1992 ); Nardello et al., *Inorg. Chem.*, 34:4950-4957 (1995 ); Aubry and Boutterny, *J. Am. Chem. Soc.*, 119:5286-5294 (1997 ); and Almeida et al., *Anal. Chim. Acta*, 482: 99-104 (2003 ).

Also included within the scope of photosensitizers are compounds that are not true sensitizers but which on excitation by heat, light, ionizing radiation, or chemical activation will release a molecule of singlet oxygen. Members of this class of compounds include, for example, the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A photosensitizer is a sensitizer for activation of a photoactive compound, for example, by generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of 200 to 1,100 nm, or 300 to 1,000 nm, or 450 to 950 nm, with an extinction coefficient at its absorbance maximum greater than 500 $M^{-1}$ $cm^{-1}$, or greater than 5,000 $M^{-1}$ $cm^{-1}$, or greater than 50,000 $M^{-1}$ $cm^{-1}$ at the excitation wavelength. Photosensitizers should be relatively photostable and may not react efficiently with singlet oxygen. Examples of photosensitizers, by way of illustration and not limitation, include acetone, benzophenone, 9-thioxanthone, eosin, 9,10-dibromoanthracene, methylene blue, metallo-porphyrins, such as hematoporphyrin, phthalocyanines, chlorophylls, rose bengal, and buckminsterfullerene, for example, and derivatives of these compounds.

A chemiluminescent compound (chemiluminescer) is a compound that is chemically activatable and, as a result of such activation, emits light at a certain wavelength. Examples of chemiluminescers, by way of illustration and not limitation, include olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as luminol; and aromatic compounds that can form endoperoxides, for example. As a consequence of the activation reaction, the chemiluminescers directly or indirectly cause the emission of light.

In certain embodiments, the singlet oxygen-activatable chemiluminescent compound may be a substance that undergoes a chemical reaction with singlet oxygen to form a metastabile intermediate species that can decompose with the simultaneous or subsequent emission of light. The composition comprising the singlet oxygen-activatable chemiluminescent compound may associate with the target analyte by any method known in the art; for example but not by way of limitation, the composition may have a second analyte-specific binding partner associated therewith that allows for the indirect association of the chemiluminescent compound to the target analyte. The composition comprising the chemiluminescent compound may be directly excited by the activated chemiluminescent compound; alternatively, the composition may further comprise at least one fluorescent molecule that is excited by the activated chemiluminescent compound.

Particular, non-limiting examples of chemiluminescent compounds and photosensitizers that may be utilized in accordance with the presently disclosed and claimed inventive concept(s) are set forth in U.S. Pat. No. 5,340,716 (Ullman, et al.), the entire contents of which are hereby expressly incorporated herein by reference.

Sensitizers utilized in accordance with the presently disclosed and claimed inventive concept(s) may be capable of indirectly binding to the target analyte via an association with streptavidin. In this manner, biotin is associated with a first analyte-specific binding partner, and the binding of streptavidin and biotin, in combination with the binding of the first analyte-specific binding partner to the target analyte, results in the indirect association of the sensitizer to the target analyte. In one non-limiting example, the sensitizer may be a photosensitizer, such that the sensitizer is activated by irradiation with light.

A singlet oxygen quencher is a compound that removes the excitation energy of the singlet oxygen species. There are two types of singlet oxygen quenchers—physical quenchers and chemical quenchers. Physical quenchers cause the removal of the excitation energy from $^1O_2$ without any chemical changes. The removal of this energy will return the oxygen molecule to its ground state energy, resulting in the reappearance of dioxygen. The energy is converted to heat, but the amount is so small that in most circumstances no detectable change in temperature will be seen. In chemical quenching, an actual chemical reaction (such as but not limited to, an "ene" reaction, a Diels-Alder type addition, addition to an activated double bond, electron transfer, etc.) occurs.

Any singlet oxygen quencher known in the art or otherwise contemplated herein may be utilized in the claimed compositions/kits/methods. The singlet oxygen quencher may possess any structure, shape and reactive groups that allow the singlet oxygen quencher to function in accordance with the presently disclosed and claimed inventive concept(s); further, the singlet oxygen quenchers utilized in accordance with the presently disclosed and claimed inventive concept(s) may quench through a chemical and/or physical mechanism. Non-limiting examples of singlet oxygen quenchers that may be used in accordance with the presently disclosed and claimed inventive concept(s) include azides; hindered amines, such as but not limited to, 1,4-diazabicyclo[2.2.2]octane (DABCO); carotenoids, such as but not limited to, β-carotene and lycopene; the amino acids cysteine, histidine, methionine, tryptophan and tyrosine, as well as peptides/proteins containing same; guanine/guanosine, as well as nucleotide sequences containing same; unsaturated fatty acids/lipids, such as but not limited to, polyunsaturated fatty acid (PUFA), cholesterol, linoleic acid, and methyl linoleate; 2,2,6,6-tetramethyl-4-piperadone (TMP); hematoporphorins; Rose Bengal; Vitamin B6; thioredoxin; ascorbate; glutathione; NADH; NADPH; and combinations and derivatives thereof. Table 1 lists exemplary singlet oxygen quenchers that may be used in accordance with the presently disclosed and claimed inventive concept(s).

In certain embodiments, the composition comprising the singlet oxygen quencher may be provided in the form of a high molecular weight composition. The singlet oxygen quencher itself may possess a high molecular weight; alternatively, a singlet oxygen quencher possessing a smaller molecular weight may be combined with other molecule(s) and/or particle(s) to provide the high molecular weight composition. The use of a high molecular weight composition prevents the interaction of the singlet oxygen quencher with the sandwich complex, and thus prevents quenching of both specific and non-specific signal; that is, the use of a high molecular weight composition prevents specific sensitizer/chemiluminescent compound interaction from being quenched by steric hindrance. Non-limiting examples of molecules/particles that may be combined with a singlet oxygen quencher to provide the high molecular weight composition include homopolypeptides containing methionine, histidine, or cysteine; heteropolypeptides containing methionine, histidine, and cysteine; naturally occurring proteins having a high content of methionine, histidine, and/or cysteine; a homopolymer or heteropolymer containing guanidine; gas soluble particles (e.g., TEFLON®, DuPont, Wilmington, Del.) and liposomes containing any of the monomeric forms of the molecules mentioned in Table 1 (below) and polymeric forms of β-carotene and lucopene; and combinations and derivatives thereof.

When a high molecular weight composition containing a singlet oxygen quencher is utilized in accordance with the presently disclosed and claimed inventive concept(s), said composition may be provided with a molecular weight of at least 100 Da. In certain embodiments, said composition may be provided with a molecular weight in a range of from about 100 Da to about 10,000,000 Da; particular non-limiting examples of molecular weight ranges for the composition include a range of from about 200 Da to about 5,000,000 Da; a range of from about 500 Da to about 2,000,000 Da; a range of from about 1,000 Da to about 1,000,000 Da; a range of from about 10,000 Da to about 500,000 Da.

TABLE 1

Quenchers of Singlet Oxygen

| Quencher | Type | $k/M^{-1}s^{-1}$ |
|---|---|---|
| Azide, $N_3$ | Physical | $2 \times 10^9$ (water) |
|  |  | $5.8 \times 10^8$ (water) |
|  |  | $5.1 \times 10^8$ ($D_2O$) |
| 1,4-diazabicyclo[2.2.2]octane (DABCO) | Physical | $1.2 \times 10^7$ (water) |
| β-carotene | Physical | $1.4 \times 10^{10}$ (solution) |
|  |  | $2 \times 10^7$ (liposomes) |
| Lycopene | Physical | $3.1 \times 10^{10}$ |
| Cysteine | Chemical | $\sim 10^7$ |
| Histidine | Chemical + Physical | $5 \times 10^7$ $\sim$75% chemical quenching |
| PUFA | Chemical | $\sim 2 \times 10^5$ |
| Ascorbate | Chemical | $3.2 \times 10^8$ |
| Methionine | Chemical | $2 \times 10^7$ |
| Guanine | Chemical | $\sim 10^6$ |

The composition containing the singlet oxygen quencher may be capable of directly or indirectly binding to sensitizer. For example but not by way of limitation, the composition may be biotinylated such that it can bind to sensitizer having streptavidin associated therewith.

The reagents of the compositions/kits/methods may be provided in any form that allows them to function in accordance with the presently disclosed and claimed inventive concept(s). For example but not by way of limitation, the reagents may be disposed in the form of single aliquot lyophilized reagents. The use of dried reagents in microfluidics devices is described in detail in co-pending application U.S. Ser. No. 61/562,677, the entire contents of which are hereby expressly incorporated herein by reference.

The presently disclosed and claimed inventive concept(s) further includes kits useful for conveniently performing an assay for the determination of an analyte; the kit may contain any combination of the above-described components/reagents; in addition, the kit may further contain other reagent(s) for conducting any of the particular assays described or otherwise contemplated herein. The nature of these additional reagent(s) will depend upon the particular assay format, and identification thereof is well within the skill of one of ordinary skill in the art.

The components/reagents may each be in separate containers/compartments, or various components/reagents can be combined in one or more containers/compartments, depending on the cross-reactivity and stability of the components/reagents. The kit can further include other separately packaged reagents for conducting an assay, such as additional sbp members, sps members and ancillary reagents, for example. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances one or more of the components/reagents in the kit can be provided as a dry powder, such as a lyophilized powder, and the kit may further include excipient(s) for dissolution of the dried reagents; in this manner, a reagent solution having the appropriate concentrations for performing a method or assay in accordance with the presently disclosed and claimed inventive concept(s) can be obtained from these components. Positive and/or negative controls may be included with the kit. The kit can further include a set of written instructions explaining how to use the kit. A kit of this nature can be used in any of the methods described or otherwise contemplated herein.

The presently disclosed and claimed inventive concept(s) is further directed to a microfluidics device that includes a sample application chamber in which a sample may be applied and an inlet channel in fluidic communication therewith that is also in fluidic communication with one or more compartments containing the three components described herein above (i.e., singlet oxygen quencher composition, sensitizer, composition comprising singlet oxygen-activatable chemiluminescent compound, or a single composition comprising both sensitizer and singlet oxygen-activatable chemiluminescent compound, as well as sensitizer or chemiluminescent composition having target analyte or an analog thereof bound thereto for use in a competitive assay format). The device may be provided with any arrangement of the compartments and distribution of the three components there between that allows the device to function in accordance with the presently disclosed and claimed inventive concept(s); non-limiting examples of device structure are provided in the Figures for illustrative purposes only.

Any of the compartments of the microfluidics device may be sealed to maintain reagent(s) disposed therein in a substantially air tight environment until use thereof; for example, compartments containing lyophilized reagent(s) may be sealed to prevent any unintentional reconstitution of the reagent. The inlet channel and a compartment, as well as two compartments, may be described as being "capable of being in fluidic communication" with one another; this phrase indicates that the compartment(s) may still be sealed, but the two compartments are capable of having fluid flow there between upon puncture of a seal formed therein or there between.

The microfluidics devices of the presently disclosed and claimed inventive concept(s) may be provided with any other desired features known in the art or otherwise contemplated herein. For example but not by way of limitation, the microfluidics devices of the presently disclosed and claimed inventive concept(s) may further include a read chamber; the read chamber may any of the compartments containing the reagents described herein above, or the read chamber may be in fluidic communication with said compartment. The microfluidics device may further one or more additional compartments containing other solutions, such as, but not limited to, wash solutions, dilution solutions, excipients, interference solutions, positive controls, negative controls, quality controls, and the like. These additional compartment(s) may be in fluidic communication with one or more of the other compartments (such as but not limited to the compartment containing the singlet oxygen quencher composition). For example, the microfluidics device may further include one or more compartments containing a wash solution, and these compartment(s) may be capable of being in fluidic communication with any other compartment(s) of the device. In another example, the microfluidics device may further include one or more compartments containing an excipient for dissolution of one or more dried reagents, and the compartment(s) may be capable of being in fluidic communication with any other compartment(s) of the device. In yet a further example, the microfluidics device may include one or more compartments containing a dilution solution, and the compartment(s) may be capable of being in fluidic communication with any other compartment(s) of the device.

In addition, any of the kits/microfluidics devices described or otherwise contemplated herein may include multiple assays multiplexed in a single kit/device. When multiple assays are present both of the assays may be constructed and function as described herein. Alternatively, an assay as described herein may be multiplexed with any other assay known in the art that is capable of being contained within the kits/microfluidics devices of the presently disclosed and claimed inventive concept(s). Non-limiting examples of other assays that may be multiplexed with the assays disclosed and claimed herein include BNP, NT-proBNP, D-Dimer, CKMB, Myoglobin, Myeloperoxidase, ST2, PCT, hCG, LH, FSH, iPTH, TSH, $fT_4$, $T_4$, PSA, fPSA, and cPSA, and combinations thereof.

When multiple assays are present in a single microfluidics device, multiple inlet channels may be connected to the sample application chamber. In certain embodiments, a portion of the sample may be passed from the sample application chamber to the multiple inlet channels without regard for the content thereof. Alternatively, structure(s) may be present in the sample application chamber, the inlet channels, and/or the connection there between that allow for separation of certain components from the whole sample and delivery of said components to the different assays. A non-limiting example of a sample distribution device that may be utilized in accordance with the presently disclosed and claimed inventive concept(s) is described in detail in Provisional Application No. 61/790,580, filed Mar. 15, 2013, entitled "Microfluidic Distributing Device."

The presently disclosed and claimed inventive concept(s) is further directed to a method for detecting the presence and/or concentration of a target analyte in a sample (such as but not limited to, whole blood, lysed whole blood cells, or red blood cells). In one embodiment, the method includes the steps of combining, either simultaneously or wholly or partially sequentially: a sample suspected of containing the target analyte with the sensitizer, composition comprising the singlet oxygen-activatable chemiluminescent compound, and the composition containing a singlet oxygen quencher as described herein above. The composition comprising the chemiluminescent compound and the sensitizer are allowed to bind to target analyte present in the sample, whereby a sandwich complex is formed, and the sensitizer is brought into dose proximity to the chemiluminescent compound. The composition comprising the singlet oxygen quencher then binds to sensitizer that is not bound in the sandwich complex. The sensitizer is then activated to generate singlet oxygen, wherein activation of the sensitizer present in the sandwich complex causes the activation of the chemiluminescent compound present in the sandwich complex. The amount of chemiluminescence generated by the activated chemiluminescent compound is then determined, and the binding, activating and determining steps may optionally be repeated for a desired number of times. The presence and/or concentration of the target analyte are detected by analyzing the amount of chemiluminescence so produced, wherein the amount of chemiluminescence is directly or inversely proportional to the amount of analyte in the sample.

In an alternative embodiment of the method of the presently disclosed and claimed inventive concept(s), the composition comprising the singlet oxygen quencher is added to the reaction mixture following the incubation step in which the sandwich complex (i.e., sensitizer, target analyte, and composition comprising the singlet oxygen-activatable chemiluminescent compound) is allowed to form.

In yet another embodiment of the method of the presently disclosed and claimed inventive concept(s), the sample suspected of containing the target analyte is combined as described above with a single composition that includes both sensitizer and singlet oxygen-activatable chemiluminescent compound. This single composition is allowed to bind to target analyte present in the sample. The singlet oxygen quencher may be added at the same time that the sample and single composition are combined, or the singlet oxygen quencher may be added after the single composition is allowed to bind to any target analyte present in the sample, whereby the singlet oxygen quencher binds to any unbound single composition. The remaining steps of the method are performed as described above for the other embodiments.

In another embodiment of the method of the presently disclosed and claimed inventive concept(s), a competitive assay format is provided. Target analyte or an analog thereof is attached to either the sensitizer or to the composition comprising single oxygen-activatable chemiluminescent compound, wherein any target analyte present in the sample competes with the sensitizer/chemiluminescent composition-bound analyte or analog thereof for binding to the other component. In these embodiments, the sample, the sensitizer, and the chemiluminescent composition are combined as described above and allowed to bind either to the target analyte or analog thereof bound to one of the two components or to target analyte present in the sample). Binding of the component containing target analyte or analog thereof to the other component forms a sandwich complex wherein the sensitizer is brought into close proximity to the chemiluminescent compound. In contrast, binding of target analyte present in the sample prevents formation of a sandwich complex that includes sensitizer and chemiluminescent compound. The singlet oxygen quencher may be added at the same time that the sample and two reagents are combined, or the singlet oxygen quencher may be added after the reagents are allowed to bind to any target analyte present in the sample, whereby the singlet oxygen quencher binds to any unbound sensitizer. The remaining steps of the method are conducted as described in the previous embodiments, with the exception that the amount of chemiluminescence is inversely proportional to the amount of target analyte present in the sample.

When the composition comprising the chemiluminescent compound includes a fluorescent molecule that is excited by the activated chemiluminescent compound, the method may further include the step of measuring the amount of light emitted by the fluorescent molecules to determine the amount of analyte in the sample.

As mentioned above, the various components of the method are provided in combination (either simultaneously or sequentially). When the various components of the method are added sequentially, the order of addition of the components may be varied; a person having ordinary skill in the art can determine the particular desired order of addition of the different components to the assay. The simplest order of addition, of course, is to add all the materials simultaneously and determine the signal produced therefrom. Alternatively, each of the components, or groups of components, can be combined sequentially. In certain embodiments, an incubation step may be involved subsequent to each addition as discussed above.

The methods of the presently disclosed and claimed inventive concept(s) may provide a heterogeneous assay; that is, certain embodiments of the method may further include one or more washing steps employed after an incubation step(s). When the reagents are added to the assay in a sequential format, the method may include multiple washing steps (i.e., after each reagent addition and incubation with the reaction). The washing steps function to reduce background signal and potentially increase analytical sensitivity. For example but not by way of limitation, one embodiment of the method may further include the step of substantially washing away unbound or non-specifically bound sample, sensitizer, composition comprising the singlet oxygen-activatable chemiluminescent compound, and composition comprising the singlet oxygen quencher from the read chamber, prior to activation of the sensitizer.

Turning now to the Drawings, FIG. 1 depicts one embodiment of a microfluidics device constructed in accordance with the presently disclosed and claimed inventive concept(s). The microfluidics device is indicated by the general reference numeral 10 and includes a housing 12 that includes a sample application chamber 14, an inlet channel 16, and a first compartment 18. A sample (such as, but not limited to, a blood sample) may be applied to the sample application chamber 14, which is in (or is capable of being in) fluidic communication with the inlet channel 16. The inlet channel 16 is in (or capable of being in) fluidic communication with the first compartment 18. The first compartment 18 contains a predetermined amount of sensitizer 20, a predetermined amount of a composition 22 that includes a singlet oxygen-activatable chemiluminescent compound, and a predetermined amount of a composition 24 (such as but not limited to, a high molecular weight composition) that includes a singlet oxygen quencher. The first compartment 18 may further be defined as a read chamber. While the sensitizer 20 and composition 22 including the singlet oxygen-activatable chemiluminescent compound are depicted in FIG. 1 as being two separate components, it will be understood that a single composition may be present in the first compartment 18 that contains both sensitizer 20 and singlet oxygen-activatable chemiluminescent compound 22. In addition, when the microfluidics device 10 is utilized in a competitive assay format, it will be understood that the target analyte or an analog thereof may be bound to one of the sensitizer 20 and the singlet oxygen-activatable chemiluminescent compound 22.

The inlet channel 16 may simply transfer a portion of the sample to the first compartment 18, or the inlet channel 16 may contain structure(s) that allow for separation of certain components from the whole sample (i.e., separation filter(s) that provide for separation of plasma or red blood cells from a whole blood sample applied to the sample application chamber 14) and/or detection of degradation (such as but not limited to, hemolysis) in the sample.

Figure 2:
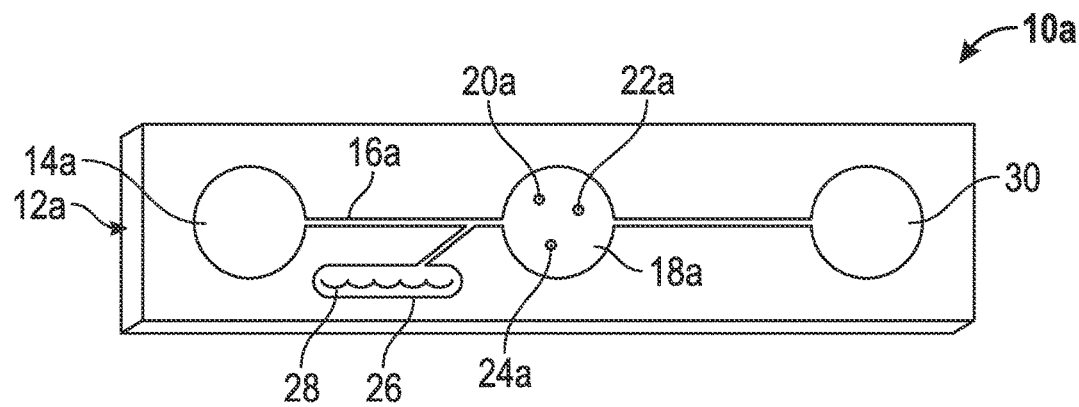
FIG. 2 illustrates a second embodiment of a microfluidics device constructed in accordance with the presently disclosed and claimed inventive concept(s).

Any of the microfluidics devices described or otherwise contemplated herein may be provided with additional compartments containing other reagents/solutions. For example, FIG. 2 depicts a microfluidics device 10a that is similar to the microfluidics device 10 of FIG. 1, with the exception that the microfluidics device 10a is provided with a heterogeneous assay format. That is, the microfluidics device 10a further includes a second compartment 26 that is in (or is capable of being in) fluidic communication with the inlet channel 16a and/or the first compartment 18a; the second compartment 26 contains a predetermined amount of wash solution 28. The microfluidics device 10a also further includes a waste compartment 30 that is in (or is capable of being in) fluidic communication with the first compartment 18a and receives the wash solution 28 once it has passed through the first compartment 18a. However, the use of a wash solution is not to be construed as limiting, and the presence within the device of any additional reagents described or contemplated herein or otherwise known in the art within one or more additional compartments also falls within the scope of the presently disclosed and claimed inventive concept(s).

Figure 3:
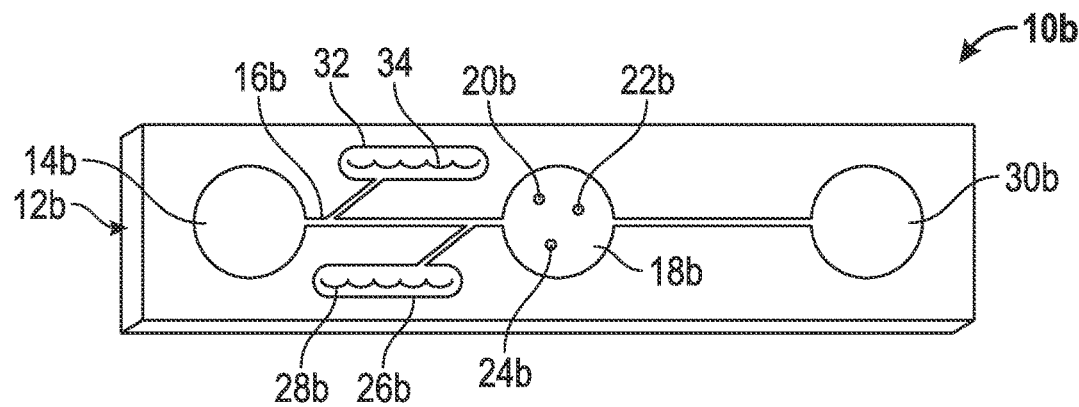
FIG. 3 illustrates a third embodiment of a microfluidics device constructed in accordance with the presently disclosed and claimed inventive concept(s).

FIG. 3 contains another example of a microfluidics device that is provided with additional compartments containing other reagents/solutions. When the reagents disposed in the compartment(s) (i.e., sensitizer, singlet oxygen-activatable chemiluminescent compound and/or solid phase-binding partner composition) are in the form of dried reagent(s), the sample/plasma may be utilized for reconstitution thereof; alternatively, the microfluidics device may be provided with one or more compartments containing excipient that may be in (or may be capable of being in) fluidic communication with one or more of the compartment(s) containing said reagent(s). In FIG. 3, a microfluidics device 10b is shown that is similar to the microfluidics devices 10 and 10a of FIGS. 1-2, except that the microfluidics device 10b further includes a third compartment 32 that is in (or capable of being in) fluidic communication with the inlet channel 16b and/or the first compartment 18b and contains a predetermined amount of excipient 34 for reconstitution of at least one of the reagents 20b, 22b, and 24b. It is to be understood that the microfluidics device 10b is illustrated as having both the second and third compartments 26b and 32 for the purposes of example only. Any of the devices disclosed or otherwise contemplated herein may be provided with the wash solution-containing compartment alone or the excipient-containing compartment alone. Alternatively, any of the devices disclosed or otherwise contemplated herein may be provided with one or more wash solution-containing compartments in combination with one or more excipient-containing compartments.

Any of the compartments of any of the microfluidics devices described or otherwise contemplated herein may be sealed to maintain reagent(s) disposed therein in a substantially air tight and/or substantially light tight environment until use thereof; for example, compartments containing lyophilized reagent(s) may he sealed to prevent any unintentional reconstitution of the reagent and/or exposure of any of the reagents to light. The inlet channel and a first compartment, as well as two compartments, may be described as being "capable of fluidic communication" with one another; this phrase indicates that the compartment(s) may still be sealed, but are capable of having fluid flow there between upon puncture of a seal formed therein.

In addition, it is to be understood that any of the microfluidics devices described or otherwise contemplated herein may further be provided with additional chambers and/or other fluidic circuits. For example but not by way of limitation, any of the microfluidics devices may additionally contain mixing chamber(s) and/or fluidic circuit(s) that are disposed between two reagent chambers.

Figure 4:
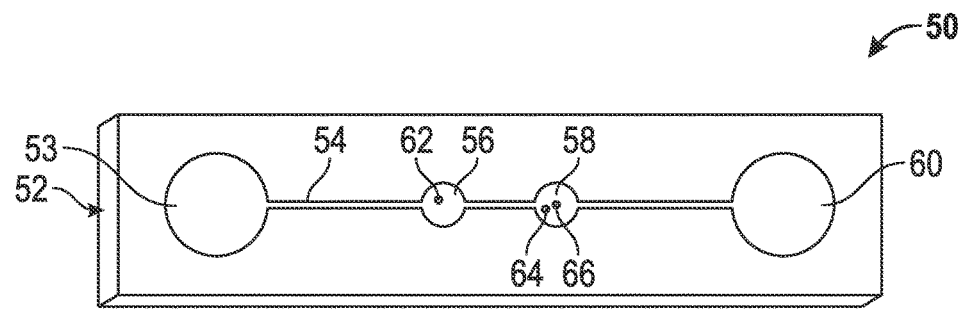
FIG. 4 illustrates another embodiment of a microfluidics device constructed in accordance with the presently disclosed and claimed inventive concept(s).

FIG. 4 depicts another embodiment of a microfluidics device constructed in accordance with the presently disclosed and claimed inventive concept(s). The microfluidics device is indicated by the general reference numeral 50 and is similar to the microfluidics devices 10, 10a, and 10b of FIGS. 1-3, except that the microfluidics device 50 contains two compartments in which the three reagents (i.e., sensitizer, singlet oxygen-activatable chemiluminescent compound, and/or singlet oxygen quencher) are disposed.

The microfluidics device 50 includes a housing 52 that includes a sample application chamber 53, an inlet channel 54, a first compartment 56, a second compartment 58, and a waste compartment 60. A sample (such as, but not limited to, a blood sample) may be applied to the sample application chamber 53, which is in (or is capable of being in) fluidic communication with the inlet channel 54. The inlet channel 54 is in (or capable of being in) fluidic communication with the first compartment 56. The first compartment 56 contains a predetermined amount of a composition 62 that includes a singlet oxygen-activatable chemiluminescent compound. The second compartment 58 is in (or is capable of being in) fluidic communication with the first compartment 56; the second compartment 58 contains a predetermined amount of a composition 64 that includes a singlet oxygen quencher and a predetermined amount of sensitizer 66. The second compartment 58 may further be defined as a read chamber and is in (or is capable of being in) fluidic communication with the waste compartment 60. In addition, when the microfluidics device 50 is utilized in a competitive assay format, it will be understood that the target analyte or an analog thereof may be bound to one of the sensitizer 66 and the singlet oxygen-activatable chemiluminescent compound 62.

The order of distribution of the reagents 62, 64, and 66 in the compartments 56 and 58 is for the purposes of example only and should not be construed as limiting. The reagents 62, 64, and 66 may be distributed in the compartments 56 and 58 in any desired order. For example, the sensitizer 66 may be disposed in the first compartment 56 along with the composition 62. Also in this manner, a single composition may be disposed in the first compartment 56 that contains both the sensitizer 66 and the composition 62. Thus, other distributions of the reagents 62, 64, and 66 in the compartments 56 and 58, as well as the combination of reagents 62 and 66 into a single reagent, also fall within the scope of the presently disclosed and claimed inventive concept(s).

In addition, the microfluidics device 50 may further be provided with one or more additional compartments containing wash solution(s) and/or excipient(s) (as described above with respect to FIGS. 2-3). When one or more additional compartments are provided, the compartments may be in (or may be capable of being in) fluidic communication with the inlet channel 54, the first compartment 56 and/or the second compartment 58.

Figure 5:
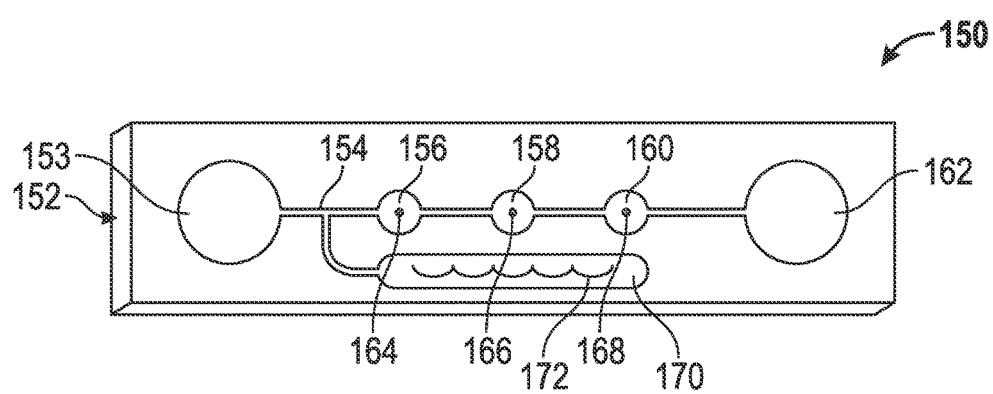
FIG. 5 illustrates another embodiment of a microfluidics device constructed in accordance with the presently disclosed and claimed inventive concept(s).

FIG. 5 depicts another embodiment of a microfluidics device constructed in accordance with the presently disclosed and claimed inventive concept(s). The microfluidics device is indicated by the general reference numeral 150 and is similar to the microfluidics devices 10, 10a, 10b, and 50 of FIGS. 1-4, except that the microfluidics device 150 contains three compartments in which the three reagents (i.e., sensitizer, singlet oxygen-activatable chemiluminescent compound and/or singlet oxygen quencher) are disposed.

The microfluidics device 150 includes a housing 152 that includes a sample application chamber 153, an inlet channel 154, a first compartment 156, a second compartment 158, a third compartment 160, and a waste compartment 162. A sample (such as, but not limited to, a blood sample) may be applied to the sample application chamber 153, which is in (or is capable of being in) fluidic communication with the inlet channel 154. The inlet channel 154 is in (or capable of being in) fluidic communication with the first compartment 156. The first compartment 156 contains a predetermined amount of a composition 164 that includes a singlet oxygen-activatable chemiluminescent compound. The second compartment 158 is in (or is capable of being in) fluidic communication with the first compartment 156; the second compartment 158 contains a predetermined amount of sensitizer 166. The third compartment 160 is in (or is capable of being in) fluidic communication with the second compartment 158; the third compartment 160 contains a predetermined amount of a composition 168 that includes a singlet oxygen quencher. The third compartment 160 may further be defined as a read chamber and is in (or is capable of being in) fluidic communication with the waste compartment 162. In addition, when the microfluidics device 150 is utilized in a competitive assay format, it will be understood that the target analyte or an analog thereof may be bound to one of the sensitizer 166 and the composition 164.

The order of distribution of the reagents 164, 166, and 168 in the compartments 156, 158, and 160 is for the purposes of example only and should not be construed as limiting. The reagents 164, 166, and 168 may be distributed in the compartments 156, 158, and 160 in any desired order.

The microfluidics device 150 is also illustrated as containing a fourth compartment 170 that contains a predetermined amount of wash solution 172. The fourth compartment 170 is illustrated as being in (or capable of being in) fluidic communication with the inlet channel 154 and/or the first compartment 156; however, it is to be understood that the fourth compartment 170 may be in for may be capable of being in) fluidic communication with any of the compartments 156, 158 and/or 160. The presence of wash solution 172 is for the purposes of example only; it is to be understood that the solution present in the fourth compartment may be excipient, or the microfluidics device may contain a fifth compartment containing excipient, as described in detail herein above. In addition, the presence of the fourth compartment 170 in the microfluidics device 150 is for purposes of example only, and it is to be understood that the microfluidics device 150 may be produced without said compartment if desired.

Figure 6:
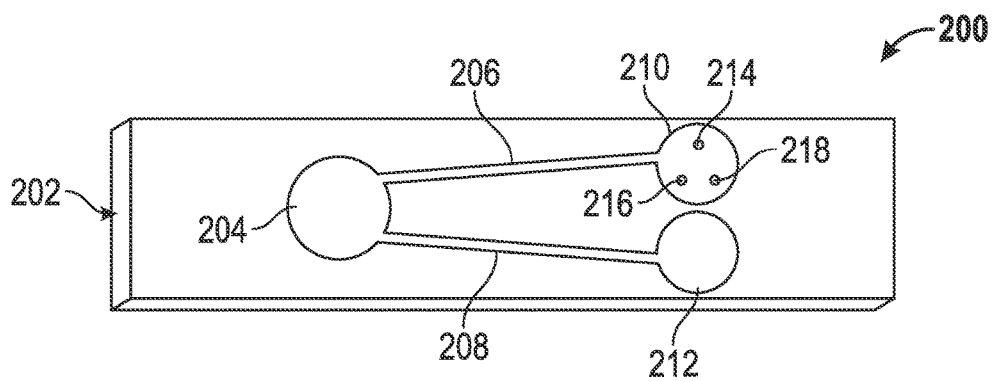
FIG. 6 illustrates yet another embodiment of a microfluidics device constructed in accordance with the presently disclosed and claimed inventive concept(s).

As stated herein above, any of the assay structures described herein above may be multiplexed with additional assay(s) in a single microfluidics device. FIG. 6 depicts another embodiment of a microfluidics device constructed in accordance with the presently disclosed and darned inventive concept(s). The microfluidics device is indicated by the general reference numeral 200 and is similar to the microfluidics devices 10, 10a, 10b, 50, and 150 of FIGS. 1-5, except that the microfluidics device 200 contains multiple compartments that provide a multiplexed assay format. The microfluidics device 200 includes a housing 202 that includes a sample application chamber 204, a first inlet channel 206, a second inlet channel 208, a first compartment 210, and a second compartment 212. A sample (such as, but not limited to, a blood sample) may be applied to the sample application chamber 204, which is in (or is capable of being in) fluidic communication with the inlet channels 206 and 208. The first inlet channel 206 is in (or capable of being in) fluidic communication with the first compartment 210. The first inlet channel 206 and the first compartment 210 represent the assay structure described in detail herein above (i.e., wherein the first compartment 210 contains a composition 214 containing a singlet oxygen-activatable chemiluminescent compound, a composition 216 containing a singlet oxygen quencher, and a sensitizer 218 wherein target analyte or an analog thereof may be bound to the composition 214 or the sensitizer 218 if the microfluidics device 200 is used in a competitive assay format). While this depicted assay structure is similar to that depicted in FIG. 1, it is to be understood that any of the other assay structures described herein above or otherwise contemplated herein may be utilized in the multiplexed assay microfluidics device. In addition, the microfluidics device 200 is provided with the second inlet channel 208 that is in (or is capable of being in) fluidic communication with the second compartment 212. The second compartment 212 is simply provided to illustrate the presence of a second assay structure; it is to be understood that multiple compartments may be present as necessary to provide the required structure associated with the second assay. In addition, it should also be understood that the second compartment 212 may be provided with reagents similar to those present in the first compartment 210, so that multiple assays detecting different analytes by the same assay mechanism are present in the same microfluidics device. Alternatively, the second compartment 212 may represent a completely different assay format; the only requirement is that this second assay format be capable of being multiplexed with one of the assays described herein.

Thus, in accordance with the presently disclosed and claimed inventive concept(s), there has been provided compositions comprising a chemiluminescent system, as well as kits and microfluidics devices containing same and methods of use thereof, that fully satisfy the objectives and advantages set forth herein above. Although the presently disclosed and claimed inventive concept(s) has been described in conjunction with the specific drawings, experimentation, results and language set forth herein above, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A chemiluminescent detection system kit comprising:
   (a) a composition comprising a singlet oxygen-activatable chemiluminescent compound that directly or indirectly binds the target analyte;
   (b) a sensitizer that directly or indirectly binds a target analyte and that generates singlet oxygen in its excited state, and wherein a sandwich complex is formed by binding of the sensitizer and the singlet oxygen-activatable chemiluminscent compound to the target analyte; and
   (c) a composition comprising a singlet oxygen quencher that interacts with unbound sensitizer but does not interact with sensitizer bound in the sandwich complex formed of chemiluminescent compound, sensitizer, and target analyte, and wherein:
      the composition comprising the singlet oxygen quencher is further defined as a high molecular weight composition comprising a singlet oxygen quencher, wherein the singlet oxygen quencher or a conjugate containing the singlet oxygen quencher has a molecular weight of at least 100 Da, and wherein steric hindrance substantially prevents the singlet oxygen quencher of the high molecular weight composition from quenching specific signal resulting from the sandwich complex.

2. The kit of claim 1, wherein the sensitizer indirectly binds the target analyte and has streptavidin associated therewith, and wherein biotin is associated with a first analyte-specific binding partner, whereby the binding of streptavidin and biotin and the binding of the first analyte-specific binding partner to the target analyte results in the indirect association of the sensitizer to the target analyte.

3. The kit of claim 1, wherein the composition comprising the singlet oxygen-activatable chemiluminescent compound has a second analyte-specific binding partner associated therewith that allows for the indirect association of the chemiluminescent compound to the target analyte.

4. The kit of claim 1, wherein the singlet oxygen-activatable chemiluminescent compound is a substance that undergoes a chemical reaction with singlet oxygen to form a metastable intermediate species that can decompose with the simultaneous or subsequent emission of light.

5. A microfluidics device, comprising:
   (a) an inlet channel through which a sample may be applied;
   (b) at least one compartment capable of being in fluidic communication with the inlet channel, the at least one compartment containing:
      (i) a composition comprising a singlet oxygen-activatable chemiluminescent compound that directly or indirectly binds a target analyte;
      (ii) a sensitizer that directly or indirectly binds the target analyte and that generates singlet oxygen in its excited state, and wherein a sandwich complex is formed by binding of the sensitizer and the singlet oxygen-activatable chemiluminescent compound to target analyte; and
      (iii) a composition comprising a singlet oxygen quencher that interacts with unbound sensitizer but does not interact with sensitizer bound in the sandwich complex formed of chemiluminescent compound, sensitizer, and target analyte, and wherein:
         the composition comprising the singlet oxygen quencher is further defined as a high molecular weight composition comprising a singlet oxygen quencher, wherein the singlet oxygen quencher or a conjugate containing the singlet oxygen quencher has a molecular weight of at least 100 Da, and wherein steric hindrance substantially prevents the singlet oxygen quencher of the high molecular weight composition from quenching specific signal resulting from the sandwich complex.

6. The microfluidics device of claim 5, wherein the sensitizer indirectly binds the target analyte and has streptavidin associated therewith, and wherein biotin is associated with a first analyte-specific binding partner, whereby the binding of streptavidin and biotin and the binding of the first analyte-specific binding partner to the target analyte results in the indirect association of the sensitizer to the target analyte.

7. The microfluidics device of claim 5, wherein the composition comprising the singlet oxygen-activatable chemiluminescent compound has a second analyte-specific binding partner associated therewith that allows for the indirect association of the chemiluminescent compound to the target analyte.

8. The microfluidics device of claim 5, further defined as comprising at least two compartments, wherein a first compartment is capable of being in fluidic communication with the inlet channel and contains (i), and wherein a second compartment is capable of being in fluidic communication with at least one of the inlet channel and the first compartment and contains (iii), and wherein (ii) is disposed in the first compartment or second compartment.

9. The microfluidics device of claim 5, further defined as comprising at least three compartments, wherein a first compartment is capable of being in fluidic communication with the inlet channel and contains (i), a second compartment in capable of being in fluidic communication with at least one of the inlet channel and the first compartment and contains (ii), and a third compartment is capable of being in fluidic communication with at least one of the inlet channel, the first compartment, and the second compartment, and wherein the third compartment contains (iii).

10. A method for detecting the presence and/or concentration of a target analyte in a sample, comprising the steps of:
  (a) combining, either simultaneously or sequentially;
    (1) a sample suspected of containing the target analyte;
    (2) a composition comprising a singlet oxygen-activatable chumiluminescent compound that directly or indirectly binds the target analyte; and
    (3) a sensitizer that directly or indirectly binds the target analyte and that generates singlet oxygen in its excited state;
  (b) allowing the binding of (2) and (3) to target analyte present in the sample, whereby a sandwich complex is formed and the sensitizer is brought into close proximity to the chemiluminescent compound;
  (c) adding a composition comprising a singlet oxygen quencher that interacts with unbound sensitizer that is not part of the sandwich complex but does not interact with sensitizer bound in the sandwich complex, and wherein:
    the composition comprising the singlet oxygen quencher is further defined as a high molecular weight composition comprising a singlet oxygen quencher, wherein the singlet oxygen quencher or a conjugate containing the singlet oxygen quencher has a molecular weight of at least 100 Da, and wherein steric hindrance substantially prevents the singlet oxygen quencher of the high molecular weight composition from quenching specific signal resulting from the sandwich complex;
  (d) activating the sensitizer to generate singlet oxygen, wherein activation of the sensitizer present in the sandwich complex causes the activation of the chemiluminescent compound present in the sandwich complex;
  (e) determining the amount of chemiluminescence generated by the activated chemiluminescent compound;
  (f) optionally repeating steps (b)-(e); and
  (g) detecting the presence and/or concentration of the target analyte by analyzing the amount of chemiluminescence so produced, wherein the amount of chemiluminescence is directly proportional to the amount of target analyte in the sample.

11. The method of claim 10, wherein the sensitizer indirectly binds the target analyte and has streptavidin associated therewith, and wherein biotin is associated with a first analyte-specific binding partner, whereby the binding of streptavidin and biotin and the binding of the first analyte-specific binding partner to the target analyte results in the indirect association of the sensitizer to the target analyte.

12. The method of claim 10, wherein the composition comprising the singlet oxygen-activatable chemiluminescent compound has a second analyte-specific binding partner associated therewith that allows for the indirect association of the chemiluminescent compound to the target analyte.

13. The method of claim 10, wherein the singlet oxygen-activatable chemiluminescent compound is a substance that undergoes a chemical reaction with singlet oxygen to form a metastable intermediate species that can decompose with the simultaneous or subsequent emission of light.

14. The method of claim 10, wherein the sensitizer is a photosensitizer and the activation of the sensitizer comprises irradiation with light.

15. The method of claim 10, wherein the composition comprising the chemiluminescent compound further comprises at least one fluorescent molecule that is excited by the activated chemiluminescent compound.

16. The method of claim 10, further comprising the step of substantially washing away unbound or non-specifically bound sample, sensitizer, singlet oxygen-activatable chemiluminescent compound and/or singlet oxygen quencher prior to activation of the sensitizer.

* * * * *